(12) United States Patent
Makino et al.

(10) Patent No.: US 7,396,922 B2
(45) Date of Patent: Jul. 8, 2008

(54) REGULATION OF HYPOXIA-INDUCIBLE GENE EXPRESSION WITH ANTISENSE INHIBITORY PAS DOMAIN PROTEIN

(75) Inventors: Yuichi Makino, Tokyo (JP); Lorenz Poellinger, Stockholm (SE)

(73) Assignee: AngioGenetics Sweden AB, Stockholm (SE)

( * ) Notice: Subject to any disclaimer, the term of this patent is extended or adjusted under 35 U.S.C. 154(b) by 153 days.

(21) Appl. No.: 10/496,945

(22) PCT Filed: Nov. 28, 2002

(86) PCT No.: PCT/SE02/02198

§ 371 (c)(1),
(2), (4) Date: Nov. 4, 2004

(87) PCT Pub. No.: WO03/045440

PCT Pub. Date: Jun. 5, 2003

(65) Prior Publication Data

US 2005/0171013 A1    Aug. 4, 2005

Related U.S. Application Data

(60) Provisional application No. 60/333,513, filed on Nov. 28, 2001.

(51) Int. Cl.
*C07H 21/04* (2006.01)
(52) U.S. Cl. .................. 536/24.5; 514/44; 536/24.31; 536/24.33
(58) Field of Classification Search .................. None
See application file for complete search history.

(56) References Cited

U.S. PATENT DOCUMENTS 5,801,154 A * 9/1998 Baracchini et al. ............ 514/44
5,998,148 A * 12/1999 Bennett et al. ................ 435/6
2002/0165140 A1  11/2002 Berkenstam et al.

FOREIGN PATENT DOCUMENTS

| WO | 98/03517 | 12/1998 |
|---|---|---|
| WO | 98/25314 | 6/1999 |
| WO | 98/25753 | 6/1999 |
| WO | 99/18539 | 2/2000 |
| WO | 00/15325 | 12/2000 |
| WO | WO 00/78341 | * 12/2000 |
| WO | 01/01334 | 8/2001 |
| WO | 01/01387 | 1/2002 |

OTHER PUBLICATIONS

American Psychological Association (APA): composition. (n.d.). The American Heritage® Dictionary of the English Language, Fourth Edition. Retrieved Jun. 7, 2007, from Dictionary.com website: http://dictionary.reference.com/browse/composition.*
Agrawal 2000, Antisense therapeutics: is it as simple as complementary base recognition? Mol. Med. Today, vol. 61, 72-81.*
Jen et al. Suppresion of Gene Expression by Targeted Disruption of Messenger RNA: Available Options and Current Strategies. Stem Cells (2000), vol. 18:307-319. AlphaMed Press.*
Opalinska et al. 2002 Nucleic-acid therapeutics: basic principles and recent applications. Nature Reviews, vol. 1, pp. 503-514).*
Gradin et al, Functional Interference between Hypoxia and Dioxin Signal Transduction Pathways: Competition for Recruitment of the Arnt Transcription Factor, Molecular and Cell Biology, vol. 16, No. 10, Oct. 1996, pp. 5221-5231.
Accession No. AI322407; Oct. 20, 1998.

* cited by examiner

*Primary Examiner*—Sean McGarry
*Assistant Examiner*—Kimberly Chong
(74) *Attorney, Agent, or Firm*—Todd E. Garabedian; Wiggin and Dana LLP

(57) ABSTRACT

A pharmaceutical composition comprises the sequence of SEQ ID NO:s 3-5 or pharmaceutically equivalent sequences. Methods employing the pharmaceutical compositions include treatments to increase angiogenesis, to stimulate HIF-1α function, to treat hypoxia-related conditions, and to maintain normal cell functions under hypoxia.

10 Claims, 17 Drawing Sheets

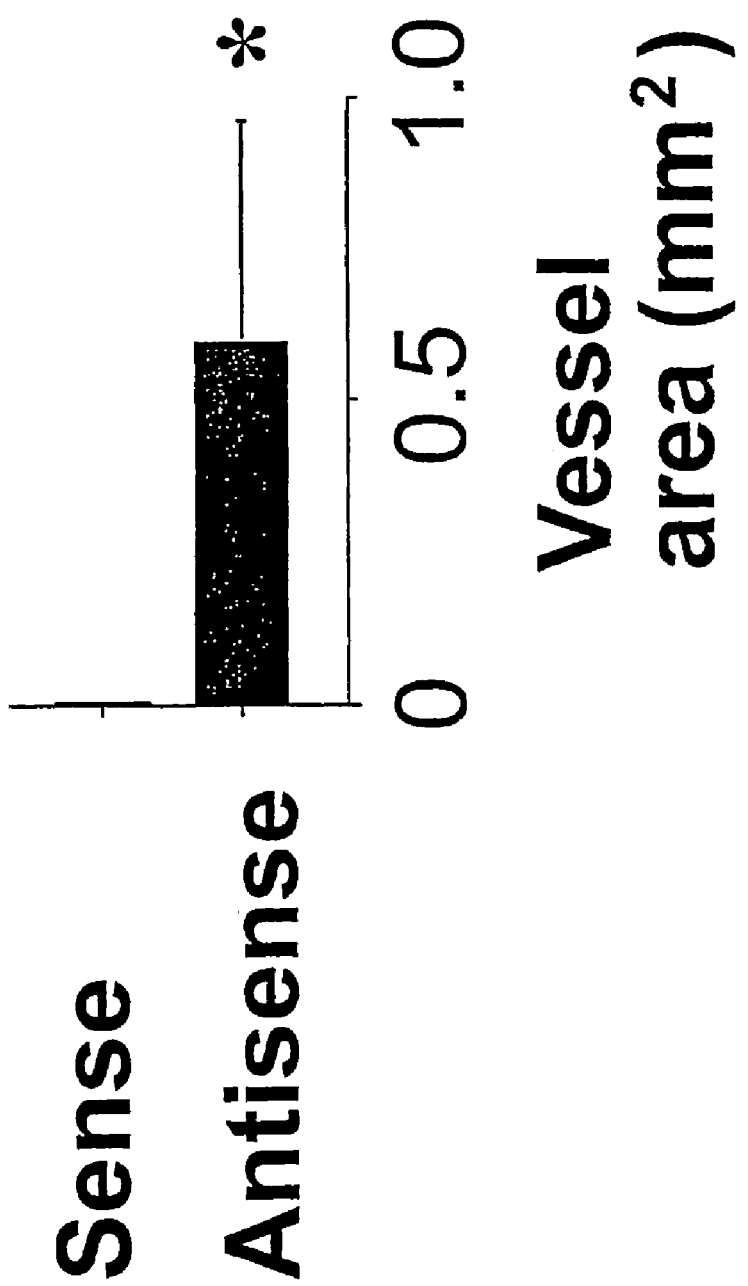

Fig. 6

```
   1   GGCACGAGGGCCATGGCGTTGGGGCTGCAGCGCGTGAGGTCGAACACCGA
  51   GCTGCGGAAGGAGAAGTCGCGGGACGCGGCCCGCAGCCGGCGCAGCCAGG
 101   AGACGGAGGTGCTGTACCAGCTGGCGCACACTCTGCCCTTTGCGCGCGGC
 151   GTCAGCGCGCACCTGGACAAGGCCTCCATCATGCGCCTCACAATCAGCTA
 201   CCTGCGCATGCACCGCCTCTGCGCAGCAGGTGGAAAAAGGGGGAGAGCCA
 251   CTGGACGCCTGCTACCTGAAGGCCCTGGAGGGTTTCGTCATGGTACTCAC
 301   CGCCGAGGGAGACATGGCTTACCTGTCGGAAAATGTCAGCAAGCACCTGG
 351   GCCTCAGTCAGTGGACCTCTGTTCCTCCTCCCTGATACATAACCCCACTC
 401   CTGGTACCAATTTCTCTCTGGAGCTCATTGGACACAGTATCTTTGATTTT
 451   ATCCATCCCTGTGACCAAGAGGAACTTCAAGACGCCCTGACCCCCAGGCC
 501   GAACCTGTCAAAGAAGAAGCTGGAAGCCCCAACAGAGCGCCACTTTTCCC
 551   TGCGAATGAAGAGCACGCTCACCAGCAGAGGGCGCACGCTCAACCTCAAA
 601   GCGGCCACCTGGAAGGTGCTGCACTGCTCAGGACATATGAGGGCCTACAA
 651   GCCCCCTGCACAGACTTCCCCTGCCGGGAGCCCTCGCTCCGAGCCTCCCC
 701   TGCAATGCCTGGTGCTTATCTGTGAAGCCATCCCCCAGCTCCCCTTCCAC
 751   GATGGTGCTACTCTGGGTCTTCCACAGGAGAAGACTCCCATCTCTACCTT
 801   ATTCACCCCTCTTTGGAAGGCACTACTTTGTCTTGTCAAGAGGTGGCCTG
 851   TTCAGGTGCTACAGGGGAAAGGGACTGAATCCTCTCTCCCCTCATGGGTG
 901   TTGTGGGCCCTTAACCGGAAAAATTGTCCTGGCTAGGAGGGAGTGAAGGA
 951   CATGGCCCAGCTATCCTTAGCCCAGAAACCCACAAATGTCTCCAAAACCA
1001   CCATAAAGACCTCTCCTTGTTAGGCACCAGAG
```

Fig. 6

```
   1  GGCACGAGGGCCATGGCGTTGGGGCTGCAGCGCGTGAGGTCGAACACCGA
  51  GCTGCGGAAGGAGAAGTCGCGGGACGCGGCCCGCAGCCGGCGCAGCCAGG
 101  AGACGGAGGTGCTGTACCAGCTGGCGCACACTCTGCCCTTTGCGCGCGGC
 151  GTCAGCGCGCACCTGGACAAGGCCTCCATCATGCGCCTCACAATCAGCTA
 201  CCTGCGCATGCACCGCCTCTGCGCAGCAGGTGGAAAAAGGGGGAGAGCCA
 251  CTGGACGCCTGCTACCTGAAGGCCCTGGAGGGTTTCGTCATGGTACTCAC
 301  CGCCGAGGGAGACATGGCTTACCTGTCGGAAAATGTCAGCAAGCACCTGG
 351  GCCTCAGTCAGTGGACCTCTGTTCCTCCTCCCTGATACATAACCCCACTC
 401  CTGGTACCAATTTCTCTCTGGAGCTCATTGGACACAGTATCTTTGATTTT
 451  ATCCATCCCTGTGACCAAGAGGAACTTCAAGACGCCCTGACCCCCAGGCC
 501  GAACCTGTCAAAGAAGAAGCTGGAAGCCCCAACAGAGCGCCACTTTTCCC
 551  TGCGAATGAAGAGCACGCTCACCAGCAGAGGGCGCACGCTCAACCTCAAA
 601  GCGGCCACCTGGAAGGTGCTGCACTGCTCAGGACATATGAGGGCCTACAA
 651  GCCCCTGCACAGACTTCCCCTGCCGGGAGCCCTCGCTCCGAGCCTCCCC
 701  TGCAATGCCTGGTGCTTATCTGTGAAGCCATCCCCCAGCTCCCCTTCCAC
 751  GATGGTGCTACTCTGGGTCTTCCACAGGAGAAGACTCCCATCTCTACCTT
 801  ATTCACCCCTCTTTGGAAGGCACTACTTTGTCTTGTCAAGAGGTGGCCTG
 851  TTCAGGTGCTACAGGGGAAAGGGACTGAATCCTCTCTCCCCTCATGGGTG
 901  TTGTGGGCCCTTAACCGGAAAAATTGTCCTGGCTAGGAGGGAGTGAAGGA
 951  CATGGCCCAGCTATCCTTAGCCCAGAAACCCACAAATGTCTCCAAAACCA
1001  CCATAAAGACCTCTCCTTGTTAGGCACCAGAG
```

REGULATION OF HYPOXIA-INDUCIBLE GENE EXPRESSION WITH ANTISENSE INHIBITORY PAS DOMAIN PROTEIN

CROSS REFERENCE TO RELATED APPLICATIONS

This application is a national stage application of International Application PCT/SE02/02198, filed Nov. 28, 2002, designating the United States of America, which claims the benefit of Provisional Application No. 60/333,513, filed Nov. 28, 2001.

FIELD OF THE INVENTION

The invention relates generally to the field of proteins related to angiogenic processes. The invention further relates to methods useful for inducing angiogenesis.

BACKGROUND OF THE INVENTION

Angiogenesis is a critical function for normal organism functioning and survival. Insufficient angiogenesis can result in cell or tissue death. Excessive angiogenesis has been linked to tumor development and other undesirable conditions. Some of the genes and biochemical processes involved in angiogenesis have been described. For example, disregulation or enhanced activation of HIF-1α function have been implicated in a variety of pathological conditions including induced tumor growth rates[9,17,18] and inflammatory angiogenesis[19]. Since it is important for organisms to maintain normal angiogenesis and for certain cells or tissues to be able to functionally counteract the activated form of HIF-1α, there remains a need in the art to provide both further information on the mechanisms that underlie angiogenesis and to present new methods useful in either increasing or decreasing angiogenesis.

SUMMARY OF THE INVENTION

It is therefore an object of the present invention to present further information related to angiogenesis and to supply novel methods to affect angiogenic responses.

According to a first embodiment of the invention, a pharmaceutical composition is provided which comprises the sequence of SEQ ID NOS:3, 4, 5, sequences complimentary to SEQ ID NO:1 or active fragments or analogs thereof. The composition may further comprise pharmaceutical carriers, adjuvants, and diluents.

According to a further embodiment of the invention, methods of increasing angiogenesis, methods of increasing HIF-1α function, methods of treating a hypoxia-related condition, and methods of maintaining normal cell or tissue function under hypoxic conditions in a cell, a group of cells, or an organism are provided, which comprise administering a pharmaceutically effective amount of a composition according to the first embodiment to the cell, group of cells, or organism. The hypoxia-related condition may be, for example, ischemia, coronary heart disease, wound healing, stroke, or diabetic ulceration.

According to a further embodiment of the invention, a plasmid is provided comprising the sequence of SEQ ID NOS:3, 4, 5, or sequences complimentary to SEQ ID NO:1. The invention also includes vectors containing such a plasmid and host cells transfected with such a vector.

According to a further embodiment of the invention, a host cell is provided which expresses the protein encoded by any one of SEQ ID NOS:3, 4, or 5.

BRIEF DESCRIPTION OF THE DRAWINGS

FIG. 2A shows a light field section of cornea after hybridization with antisense RNA probes of mIPAS;

FIG. 2B shows a dark field section of cornea after hybridization with antisense RNA probes of mIPAS;

FIG. 2C shows a light field section of cornea after hybridization with antisense RNA probes of mHIF-1α;

FIG. 2D shows a dark field section of cornea after hybridization with antisense RNA probes of mHIF-1α;

FIG. 2E shows a light field section of retina after hybridization with antisense RNA probes of mIPAS;

FIG. 2F shows a dark field section of retina after hybridization with antisense RNA probes of mIPAS;

FIG. 2G shows a light field section of retina after hybridization with antisense RNA probes of mHIF-1α;

FIG. 2H shows a dark field section of retina after hybridization with antisense RNA probes of mHIF-1α;

FIG. 2I shows a light field section of cerebellum after hybridization with antisense RNA probes of mIPAS;

FIG. 2J shows a dark field section of cerebellum after hybridization with antisense RNA probes of mIPAS;

FIG. 2K shows a light field section of cerebellum after hybridization with antisense RNA probes of mHIF-1α;

FIG. 2L shows a dark field section of cerebellum after hybridization with antisense RNA probes of mHIF-1α;

FIG. 4 shows IPAS expression in hepatoma cells retards tumor growth, specifically, FIG. 4A shows increases in tumor volumes after subcutaneous implantation of wild-type Hepa1c1c7 or Hepa IPAS cells in immunodeficient SCID mice, where the asterisk indicates ($p<0.001$) difference in results between the two cell lines and a double asterisk indicates a difference of ($p<0.01$);

FIG. 5E results of ocular angiogensis studies presenting the mean ±SD area of neovascularisation, where an asterisk represents a difference of (p<0.001) between the scrambled and sense oligonucleotide treated groups;

FIG. 6 shows the full length IPAS DNA sequence (SEQ ID NO:2).

DETAILED DESCRIPTION

Alteration of gene expression is a crucial component of adaptive responses to hypoxia. These responses are mediated by hypoxia-inducible transcription factors (HIFs)[1,2]. A novel basic helix-loop-helix (bHLH)/PAS protein related to HIFs was identified by methods detailed below and termed Inhibitory PAS (Per/Arnt/Sim) domain protein, or IPAS. IPAS was found to contain no transactivation function and demonstrated dominant negative regulation of HIF-mediated control of gene expression. Ectopic expression of IPAS in hepatoma cells selectively impaired induction of genes involved in adaptation to a hypoxic environment, notably the vascular endothelial growth factor (VEGF) gene. It also resulted in retarded tumor growth and reduced tumor vascular density in vivo.

IPAS shows predominantly nuclear localization under both normoxic and hypoxic conditions, as assessed by green fluorescent fusion protein assays (data not shown). As described more fully below, IPAS was predominantly expressed in mice in Purkinje cells of the cerebellum and in corneal epithelium of the eye. Expression of IPAS in the cornea correlated with low levels of expression of the VEGF gene under hypoxic conditions. Strikingly, application of an IPAS antisense oligonucleotide to the mouse cornea induced angiogenesis under normoxic conditions, and unmasked hypoxia-dependent induction of VEGF gene expression in hypoxic cornea cells. These unexpected results indicate a novel mechanism for negative regulation of angiogenesis and maintenance of an avascular phenotype.

EXAMPLE 1

Isolation of IPAS cDNA and Creation of Antisense IPAS Expression Plasmid

Hidden Marcov Model profiles[3] for HIF homology were built using the HMMER 1,8,3 software[21] from nucleotide sequences corresponding to the PAS domain of a selected number of bHLH/PAS factors. The model profiles were used to search mouse expressed sequence tag (EST) databases. An EST clone encoding a putative novel protein and containing a bHLH PAS motif was identified (Gene Bank accession # AA028416) and was subsequently obtained, sequenced and designated IPAS.

Figure 1A:
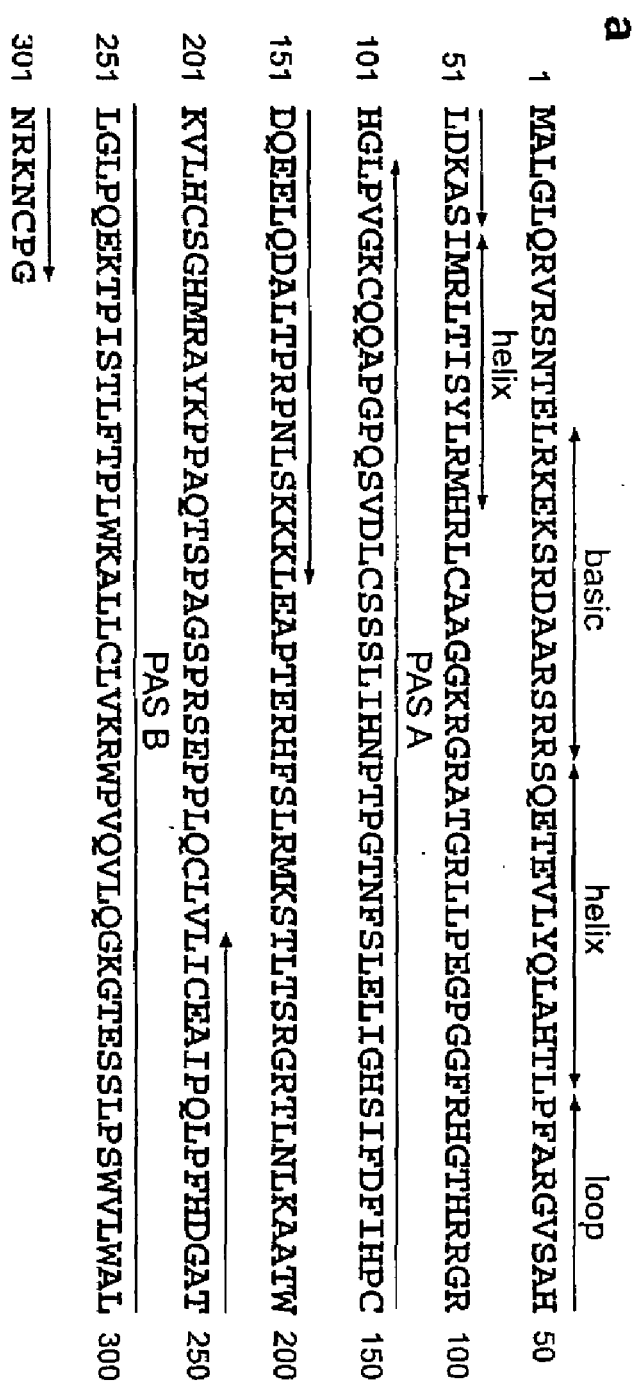
FIG. 1A shows the deduced amino acid sequence of mouse IPAS (SEQ ID NO:1)
Figure 1B:
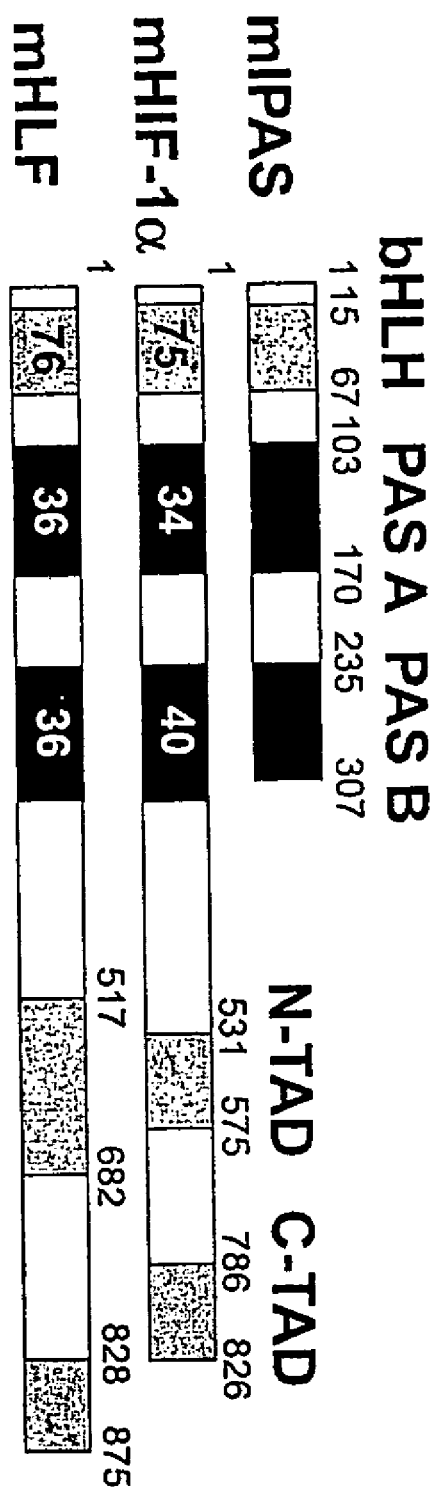
FIG. 1B is a diagram representing a comparison between mouse IPAS, mouse HIF-1α, and mouse HLF/EPAS1 with percent identities.

The nucleotide sequence for IPAS is provided at SEQ ID NO:2 (FIG. 6). DNA sequence analysis revealed that IPAS cDNA contains an open reading frame of 921 nucleotides, encoding a polypeptide of 307 amino acids (FIG. 1A, SEQ ID NO:1). Alignment analysis of the amino acid sequence with known bHLH PAS factors showed high similarity to HIF-1α[4] and HLF/EPAS1[5,6] in the N-terminal bHLH domain (75% and 76% identity, respectively; FIG. 1B), and to a lesser extent within the PAS region (34% and 36% in the PAS A, and 40% and 36% in the PAS B domain. respectively; FIG. 1B). Notably, IPAS was found to lack the sequence corresponding to C-terminal region of HIF-1α and HLF/EPAS1, in which two transactivation domains (N-TAD and C-TAD) have been previously identified (FIG. 1B).

pcDNA3 IPAS was constructed by inserting an EcoRl-Not I fragment from pT7T3D IPAS (Gene Bank accession #AA028416) into pcDNA3 (Invitrogen). The resulting vector was then used to subclone IPAS into the pCMV FLAG vector[22], pGEX-4T-3 (Amersham-Pharmacia Biotec), pCMX GAL4, or pCMX VP-16, to create expression vectors for GST, GAL4, or VP16 fusion proteins, respectively. Full length IPAS cDNA was inserted in an inverted direction into pcDNA3, constructing an antisense IPAS expression plasmid.

EXAMPLE 2

Cell Culture and Transfection Experiments

IPAS-expressing HEPA cells (Hepa IPAS cells) were established by stable transfection of mouse hepatoma Hepal-clc7 cells (ATCC) with pEFIRESpuro IPAS and puromycin (5 µg/ml) selection. In luciferase reporter gene assays, 0.5 µg of reporter plasmid and indicated amounts of expression plasmids were used for transfection by lipofection. Conditions for hypoxia or TCDD treatment of the cells have been previously reported[16]. Protein expression Was monitored in whole cell extracts by immunoblot assays using HIF-1α (Novus), HLF/EPAS1 (Novus), and FLAG epitope (Sigma) antibodies essentially as previously reported[8,22].

Figure 3A:
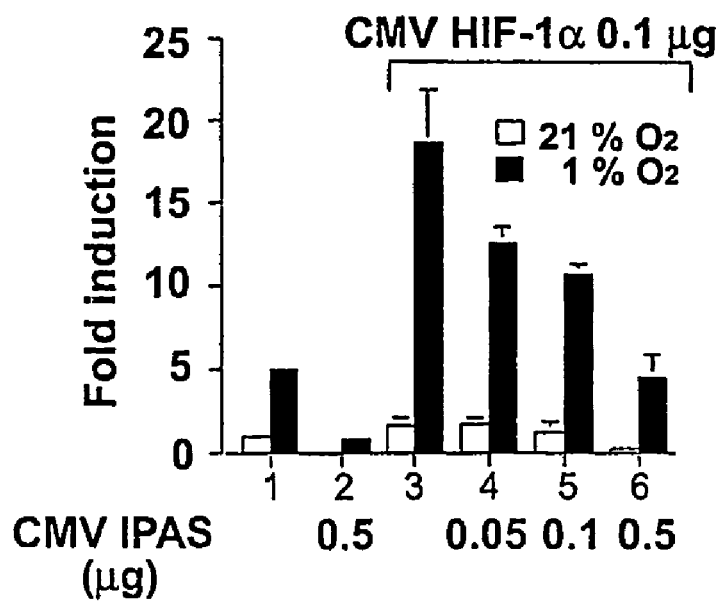
FIG. 3A shows IPAS inhibition of HIF mediated reporter gene activation in hypoxic HeLa cells.
Figure 3B:
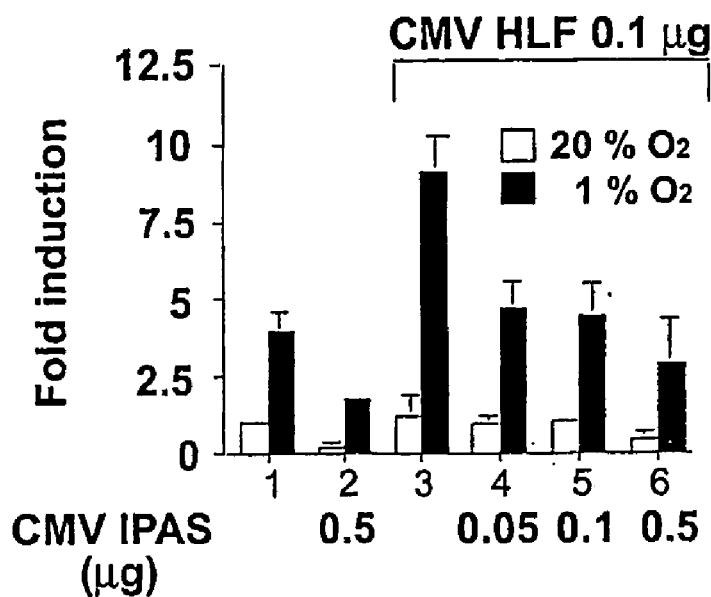
FIG. 3B shows IPAS inhibition of HLF/EPAS1 mediated reporter gene activation in hypoxic HeLa cells.
Figure 3C:
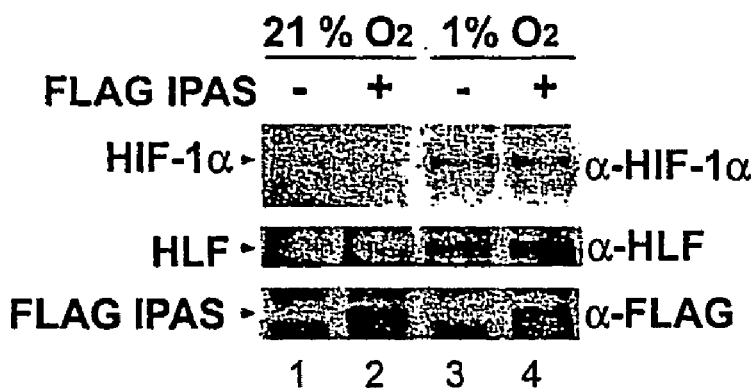
FIG. 3C shows that HIF-1α and HLF protein stability are not affected by IPAS in HeLa cells.
Figure 3D:
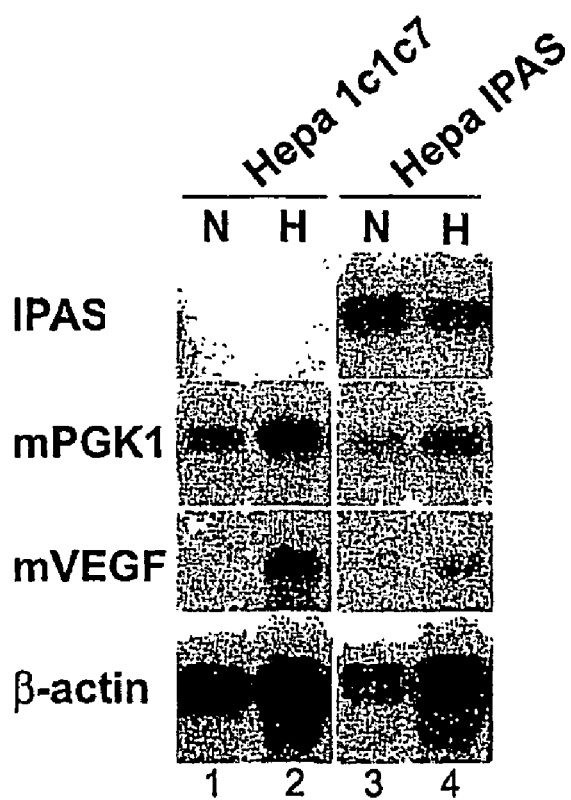
FIG. 3D demonstrates hypoxia-inducible gene expression impairment by IPAS overexpressing cells.

IPAS mRNA expression was not detected in the wild-type cells (FIG. 3D). Under hypoxic conditions these cells showed markedly increased expression of phosphoglycerate kinase1 and VEGF mRNA expression, as expected[11,12]. In response to hypoxia, Hepa IPAS cells showed decreased levels of hypoxia-dependent activation of these genes (45% and 48% reduction of the induction response, respectively; FIG. 3D). This IPAS-mediated effect was at the transcriptional level, since activation of a transiently transfected HRE-driven reporter gene by hypoxia was significantly lower in Hepa IPAS cells than in wild-type cells (data not shown). Reporter gene activation was even suppressed in Hepa IPAS cells following transient overexpression of HIF-1α, indicating that IPAS impairs productive interaction between HIF-1α and the HRE.

Figure 3E:
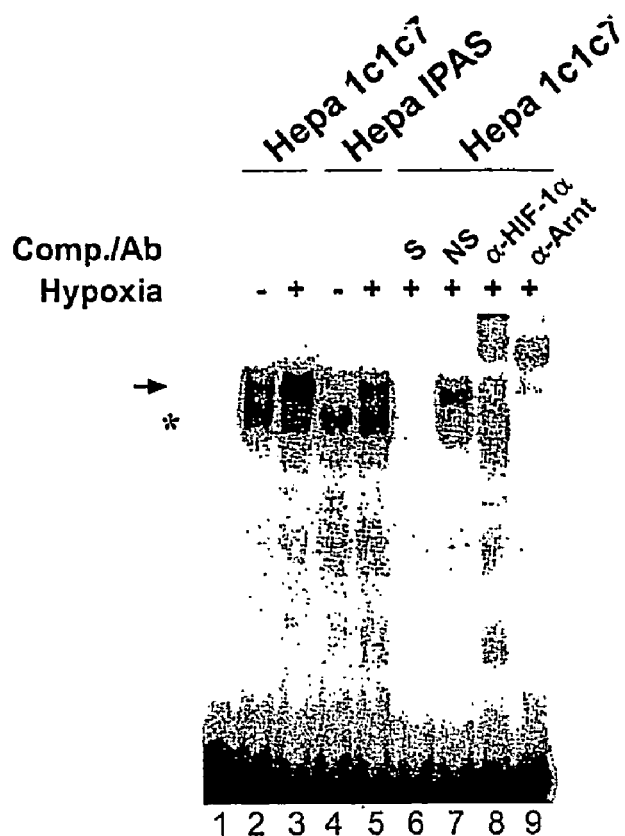
FIG. 3E shows IPAS inhibition of the DNA binding activity of HIF-1α, where the asterisk indicates constitutive HRE binding activity, the arrow indicates a HIF-1α/Arnt-DNA complex, S indicates unlabeled HRE control and NS indicates unrelated sequence control.

HRE-specific DNA binding activity by the HIF-1α/Arnt heterodimeric complex was lower in nuclear extracts from either normoxic or hypoxic IPAS-expressing cells than in corresponding nuclear extracts from wild-type cells (FIG. 3E). The dioxin (aryl hydrocarbon) receptor which mediates gene regulation in response to xenobiotic chemicals is also a member of the bHLH/PAS transcription factor family and shares the dimerisation partner factor Arnt with HIF-1α[13]. In contrast to hypoxia-inducible gene expression, dioxin-induced expression of dioxin receptor target gene cytochrome P-4501A1 was not perturbed in the Hepa IPAS cells (data not shown).

Six week-old C57B16/J healthy mice sacrificed by a lethal dose of $CO_2$ and their primary corneal epithelial cells were isolated. The eyes were enucleated and the corneal tissue was dissected in DME medium supplemented with 10% bovine calf serum under a stereomicroscope. Tissue masses were placed onto a gelatin-coated tissue culture plate and incubated in the same media supplemented with 3 ng/ml human recombinant FGF-β. After incubation for 8 days, corneal epithelial cells were trypsinised, and single cell suspensions were used for subsequent assays.

EXAMPLE 3

IPAS Regulation of Transcriptional Responses to Hypoxia

Due to the structural similarity of IPAS to HIFs and the colocalization of IPAS and HIF-1α in mouse cornea the putative role of IPAS in regulation of transcriptional responses to hypoxia was investigated. A transient transfection assay was performed in HeLa cells (ATCC) using a hypoxia-response element (HRE) driven luciferase reporter gene in the absence or presence of transiently expressed IPAS. In the absence of IPAS, incubation of the cells under hypoxic (1% $O_2$) conditions resulted in induction of reporter gene activity, reflecting the induced transactivation function of endogenous HIFs. Transient expression of IPAS reduced this hypoxia-inducible activation response (FIGS. 3A, 3B).

Hypoxia-dependent activation of the reporter gene by coexpression of either HIF-1α (FIG. 3A) or HLF/EPAS1 (FIG. 3A) was impaired in a dose-dependent manner by IPAS. IPAS acts as a dominant negative regulator of HIF-1α and HLF/EPAS1-mediated gene expression. IPAS had no effect on hypoxia-induced protein stabilization of HIF-1α and HLF[7,10] (FIG. 3C) indicating that IPAS targeted regulatory steps located further down-stream than protein stabilization in HIF-mediated signal transduction.

EXAMPLE 4

RNA Blot and in situ Hybridization Analysis

Poly(A)+RNA samples (4.5 μg) were collected from a variety of C57B16 mouse tissues, Hepa1c1c7 and Hepa IPAS cells using the guanidiumthiocyanate method. The samples were purified using oligodT (Dynal). The purified samples were analyzed by northern blot analysis using $^{32}P$-labeled cDNA probes of mIPAS (nt 623-897), mPGK1 (nt 426-771), mVEGF3 (nt 24-466), mCYP1A1 (nt 874-1199), and mβ-actin (nt 930-1075).

Figure 1C:
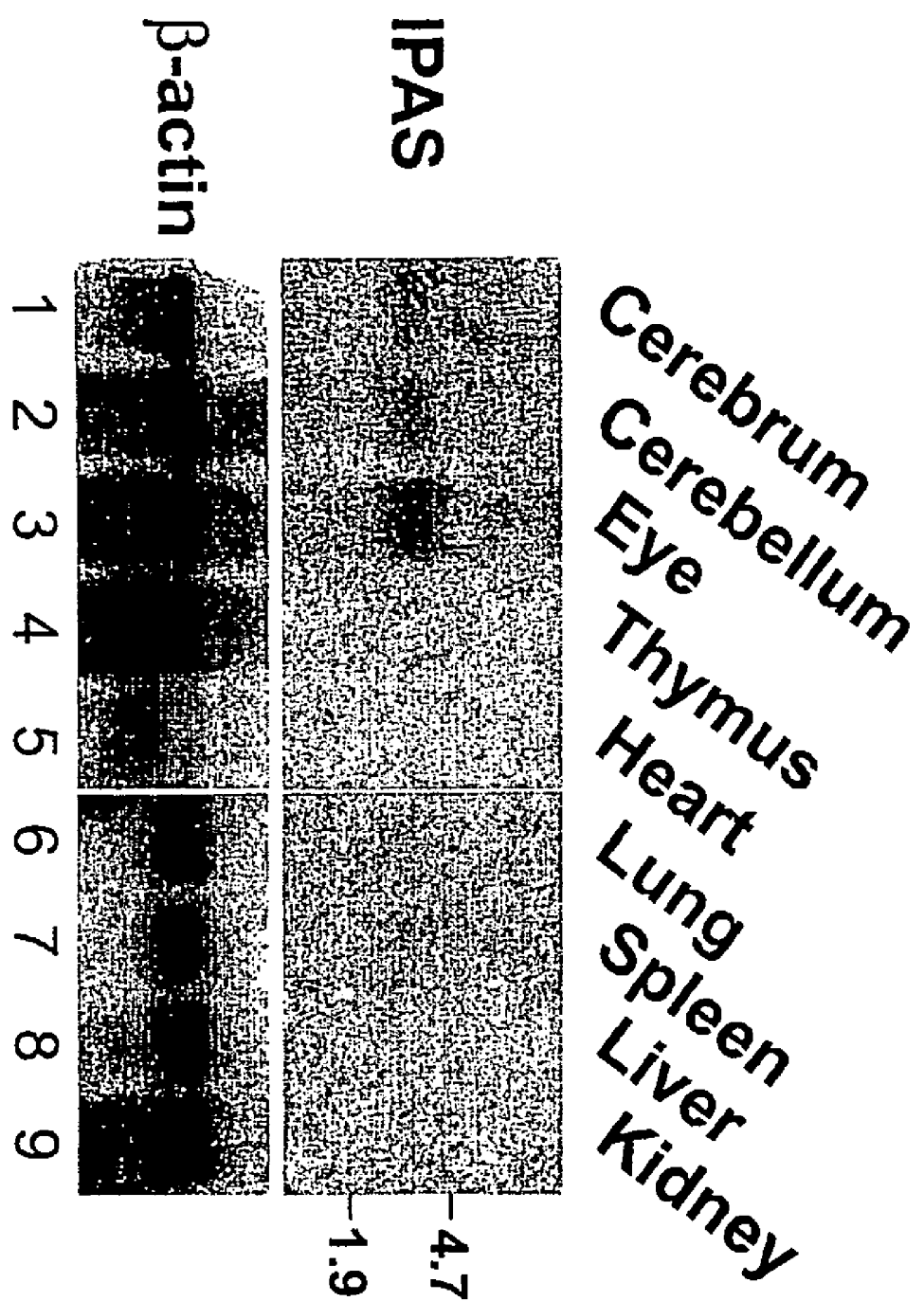
FIG. 1C shows the results of a RNA blot analysis of IPAS expression in adult mice tissues.

The results of the analysis of mouse tissue samples demonstrated that IPAS was expressed predominantly in the eye and at lower levels in the cerebellum and the cerebrum. No expression was detected in other tested mouse tissues, indicating a tissue-restricted expression pattern of IPAS mRNA (FIG. 1C).

In situ hybridization assays of tissue samples from 8 week-old C57B16 mice were performed to characterize the spatial expression pattern of IPAS in the eye and cerebellum. The in situ hybridizations were conducted using $^{35}S$-labeled mIPAS or mHIF-1α antisense RNA probes according to known methods[23].

Figure 2:
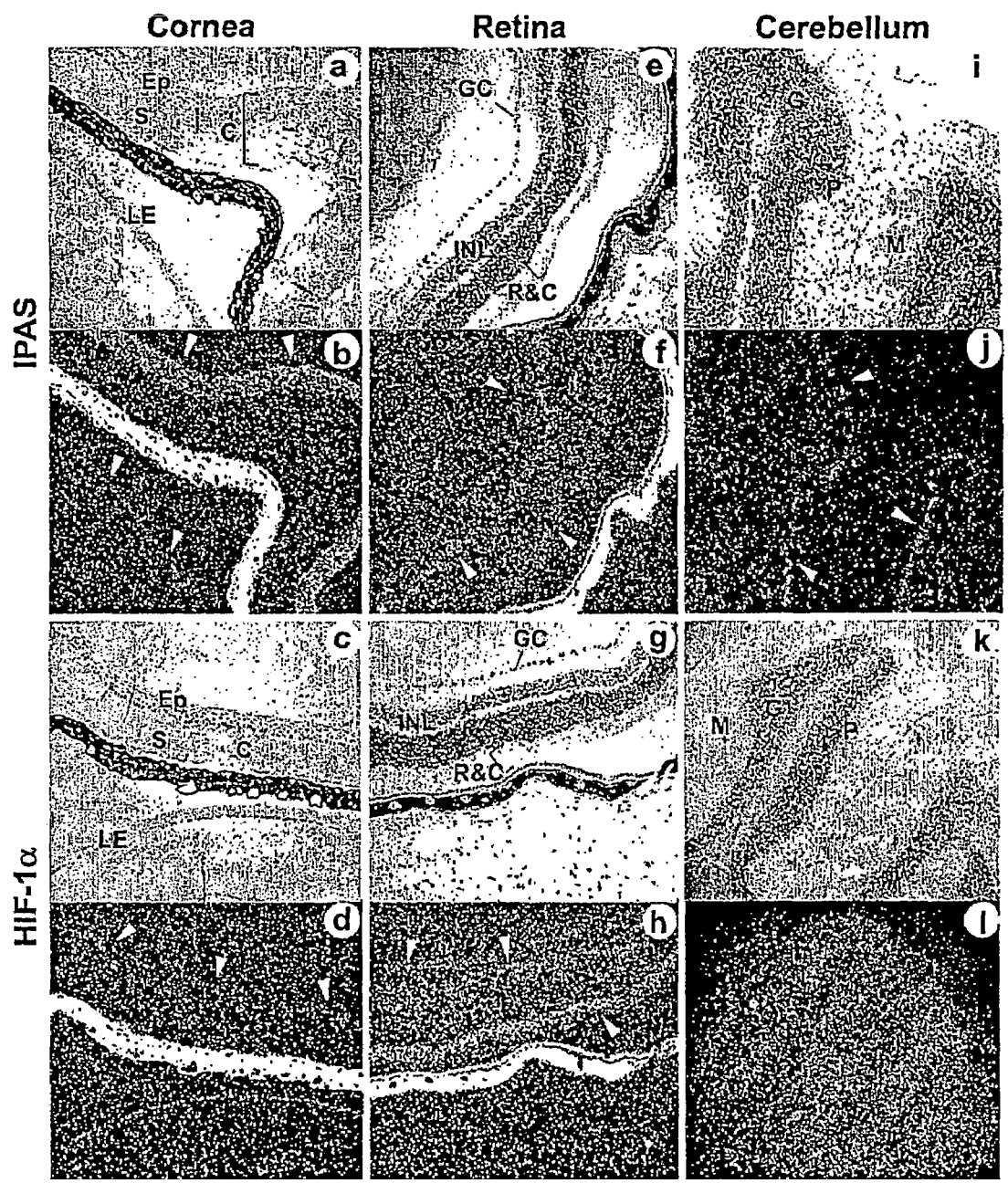
FIG. 2 shows the results of an in situ hybridization analysis of IPAS expression in selected regions of adult mice, specifically.

Intense IPAS expression was observed in the epithelial cell layer of the cornea (FIGS. 2A, 2B) and with lower intensity in the layers of ganglion cells, inner nuclear cells, and rods and cones of the retina (FIGS. 2E, 2F). Expression of HIF-1α mRNA was detected at low levels in the epithelium of the cornea (FIGS. 2C, 2D), demonstrating dominant expression of IPAS over HIF-1α in these cells. HIF-1α was also expressed in the same layers of retina where IPAS expression was observed (FIGS. 2G, 2H). In the cerebellum, expression of IPAS was limited to the Purkinje cell layer (FIGS. 21, 2J). HIF-1α did not show any similar spatially defined expression throughout the sections (FIGS. 2K, 2L). Both IPAS and HIF-1α mRNAs were detected as weak diffuse signals over nonspecific background levels in certain areas of the cerebrum (data not shown).

EXAMPLE 5

Electrophoretic Mobility Shift and in vitro Protein Interaction Assays

Nuclear extracts from either normoxic or hypoxic cells were prepared and analyzed by electrophoretic mobility shift assays as known in the art[16]. GST-IPAS or GAL4 fusion proteins spanning various fragments of HIF-1α were generated by translation either in the presence or absence of $^{35}S$-labeled methionine in rabbit reticulocyte lysate (Promega). Equal concentrations of $^{35}S$-labeled, in vitro translated Arnt, HIF-1α or IPAS were incubated with GST-IPAS or GAL4HIF-1α fusion proteins for 1 hour at room temperature. Afterward, the proteins were incubated with anti-GST (Amersham-Pharmacia Biotech) or anti-GAL4 (Upstate Biotechnology) antibodies coupled to Protein A-Sepharose (Amersham-Pharmacia Biotech) for 1 hour at room temperature. After brief centrifugation, coimmunoprecipitated proteins were analyzed by SDS polyacrylamide gel electrophoresis and autoradiography.

EXAMPLE 6

Assays for IPAS Interaction with HIF-1α or Arnt

Figure 3F:
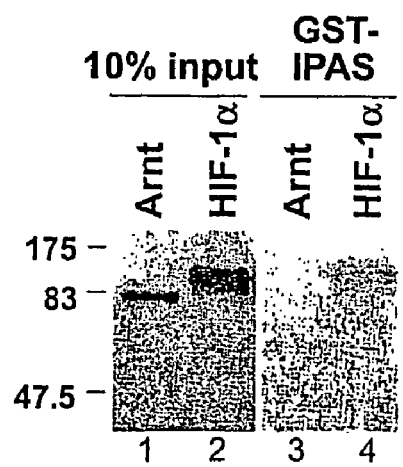
FIG. 3F shows immunoprecipitation with anti-GST antibodies revealing that GST IPAS physically interacts with in vitro translated HIF-1α.
Figure 3G:
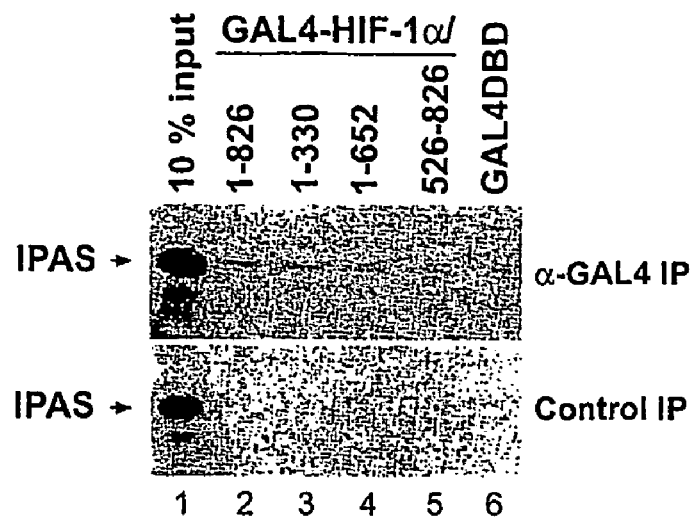
FIG. 3G represents a coimmunoprecipitation of $^{35}$S-labeled IPAS with GAL4-fused HIF-1α fragments by anti-GAL4 antibodies showing the N-terminus of HIF-1α mediating heterodimerisation with IPAS.

Coimmunoprecipitation assays were conducted to examine whether the inhibitory action of IPAS was mediated by direct interaction with HIF-1α or Arnt. Glutathione S-transferase-(GST-) IPAS fusion protein was coprecipitated with HIF-1α but not with Arnt, demonstrating specific physical interaction between IPAS and HIF-1α (FIG. 3F). The assays further demonstrated that the N-terminal structures of HIF-1α (amino acids 1-330, mainly composed of the bHLH/PAS motif) mediated association with IPAS (FIG. 3G).

Figure 3H:
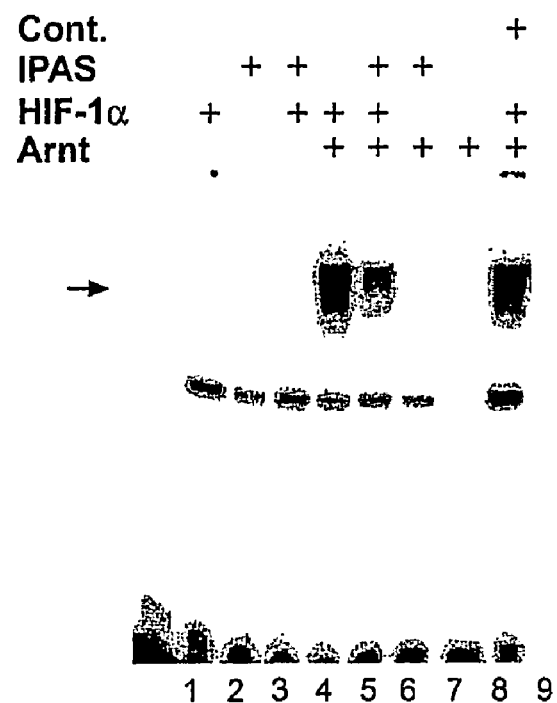
FIG. 3H shows how combinations of in vitro translated IPAS, HIF-1α, Arnt, or control lysate were analyzed to reveal that the IPAS/HIF-1α heterodimer fails to bind the HRE sequence motif.

Mammalian two-hybrid assays employing a GAL4 fusion protein spanning the bHLH/PAS domain of HIF-1α as a bait demonstrated interaction with an IPAS-VP16 fusion protein. Consistent with the in vitro precipitation experiments, GAL-4-IPAS failed to show any interaction with Arnt-VP16 in vivo (data not shown). The IPAS/HIF-1α complex was inert with regard to binding to an HRE probe. The HRE binding activity of HIF-1α/Arnt heterodimer was impaired upon exposure to IPAS (FIG. 3H). Both of these results are consistent with the reduced levels of HIF-1α-dependent DNA binding activity observed in nuclear extracts of cells stably expressing IPAS (FIG. 3E).

EXAMPLE 7

Investigation of Role of IPAS in Corneal Epithelium

The cornea is an interesting study target because the transparency required for clear vision is present only with total avascularity. It is known that hypoxic conditions exist in the corneal environment following overnight closure of the eye during sleep[14,15]. The levels of hypoxia reached in the cornea would be sufficient to stimulate HIF-1α-dependent gene expression in other cell types. However, such a gene activation response and neovascularization of the cornea do not normally occur, suggesting a mechanism of negative regulation.

Figure 5A:
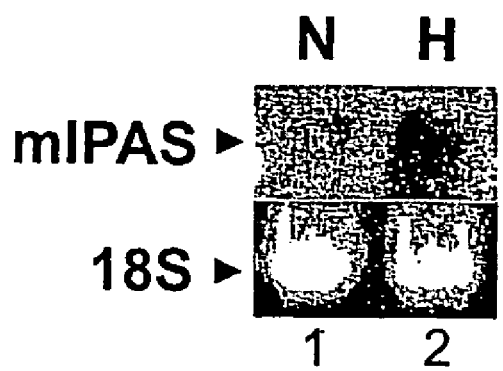
FIG. 5A shows IPAS expression in primary cultures of mouse cornea epithelium cells using RNA blotting following incubation under normoxic or hypoxic conditions for 24 hours.

Analysis of VEGF mRNA expression in primary cultures of mouse cornea epithelium cells was conducted to ascertain whether IPAS plays such a role in negative regulation of VEGF expression in the cornea. A low but detectable level of IPAS mRNA expression under normoxic conditions was detected. Exposure of the cells to hypoxia for 24 hours resulted in enhanced IPAS mRNA expression levels (FIG. 5A).

Non-corneal mice tissues were exposed to hypoxia (6% $O_2$) for 6 hours to assess hypoxia-induced IPAS expression regulation. Consistent with other experimental results (FIG. 1C), very low levels of IPAS expression were observed in most tissues of control mice kept at normoxia. In addition to corneal cells, IPAS mRNA expression was induced by hypoxia (2.2- to 3.9-fold induction) in the cerebrum, cerebellum, heart, and skeletal muscle (FIG. 5B), suggesting IPAS may modulate hypoxia-inducible gene regulatory responses in these tissues under conditions of hypoxia or ischemia.

Figure 5F:
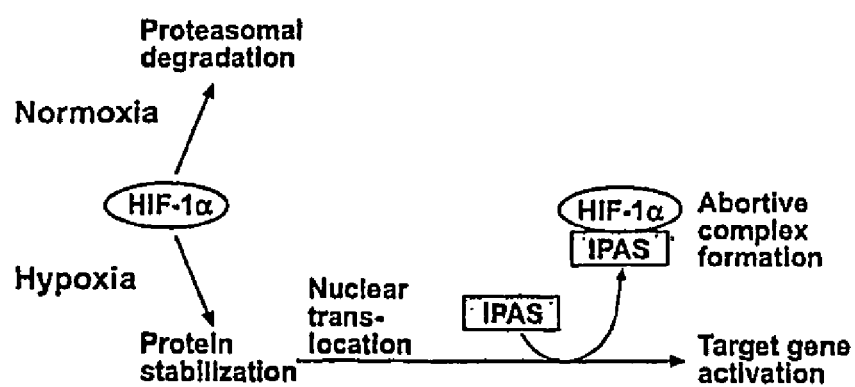
FIG. 5F is a schematic model of the negative regulation of HIF-1α function by IPAS.
Figure 5B:
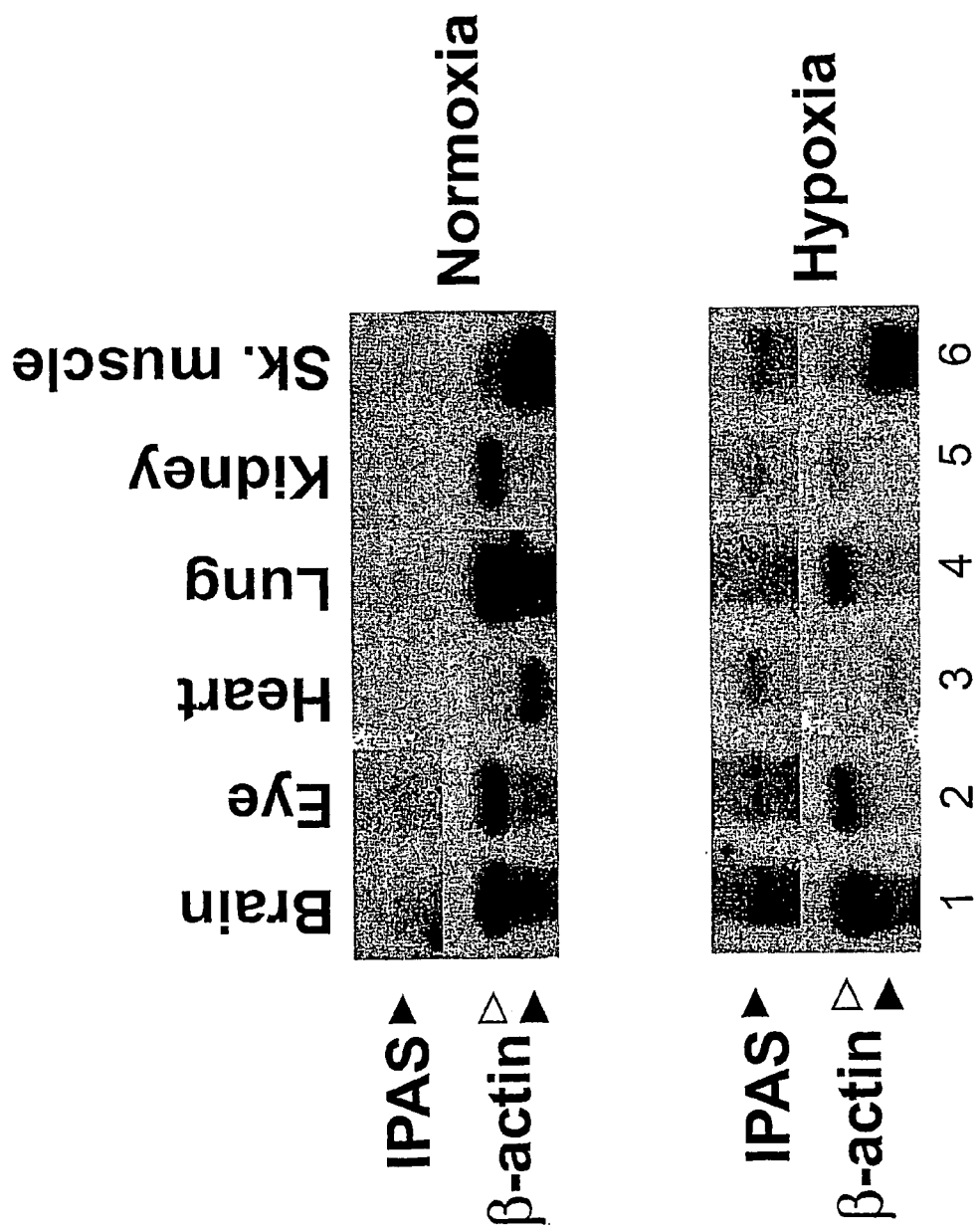
FIG. 5B shows hypoxia inducible expression of IPAS mRNA in mouse tissues, where the white arrow indicates a 2.0 kb form of β-actin and a black arrow indicates a 1.8 kb form of β-actin.
Figure 5C:
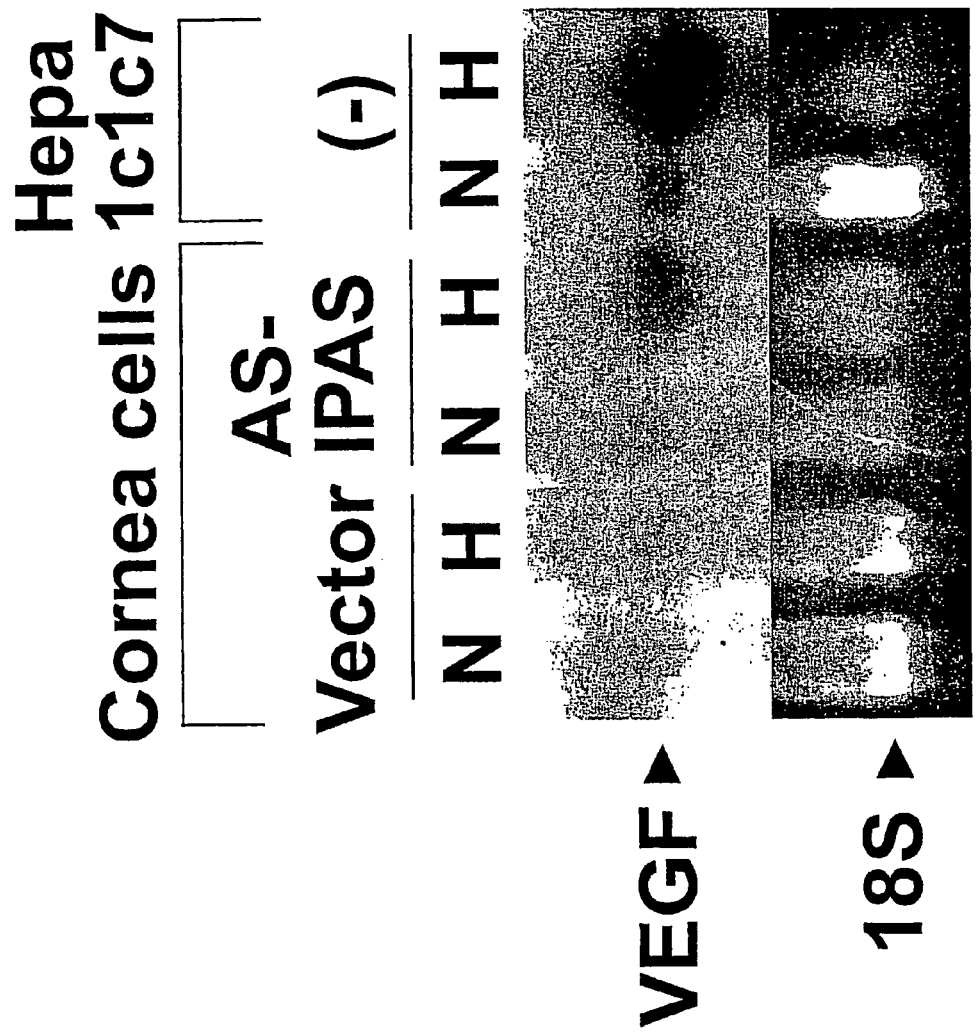
FIG. 5C shows VEGF mRNA expression in hepatoma or primary cornea cells transfected with control or antisense IPAS vectors.

In contrast to wild-type mouse Hepa1c1c7 cells[16], primary cornea cells were transfected with an empty expression vector and demonstrated almost undetectable basal levels of VEGF mRNA expression. Hypoxia produced only a very modest induction response (FIG. 5C).

Primary cornea cells were transiently transfected with an antisense IPAS expression vector to down-regulate IPAS expression levels. The introduction of the antisense IPAS vector resulted in elevation of basal VEGF mRNA expression levels and significant hypoxia-inducible expression of the VEGF gene (FIG. 5C), showing IPAS has an important role in negative regulation of both basal level expression and hypoxia-dependent activation of the VEGF gene in cornea epithelium.

EXAMPLE 8

Mouse Corneal Micropocket Assay and Hypoxic Exposure of Mice

The mouse corneal angiogenesis assay was performed as previously reported[24]. Slow release micropellets of sucrose aluminium sulfate and hydron polymers containing 2.5 µg of phosphorothioate-coupled IPAS antisense (5'-TCACGCGCTGCAGCCCCAAC GCCAT-3') (SEQ ID NO:3), sense (5'-ATGGCGTTGGGGCTGCAGCG CGTGA-3') (SEQ ID NO:4), or scrambled oligonucleotides were implanted into corneal pockets of 6 week-old male C57B16/J mice. The full length IPAS antisense sequence is provided in SEQ ID NO:5. Alternate sequences of these or any other disclosed or claimed sequence may be employed. Alternate sequences include functional fragments and analogs, or entities having acceptable levels of homology with the specific sequence described. Construction and use of alternate sequences is known in the art.

Six mice and 12 corneas were used in each group. The vascular area of the corneas of all the mice was measured by slit-lamp stereomicroscopy on day 5 after pellet implantation, and statistically evaluated by Student's two-tailed t-test. In hypoxia experiments eight week-old mice were either kept at normoxia or exposed to normobaric hypoxia (6% $O_2$) for 6 hours in an airtight chamber flushed with a mixture of nitrogen and room air.

Figure 5D:
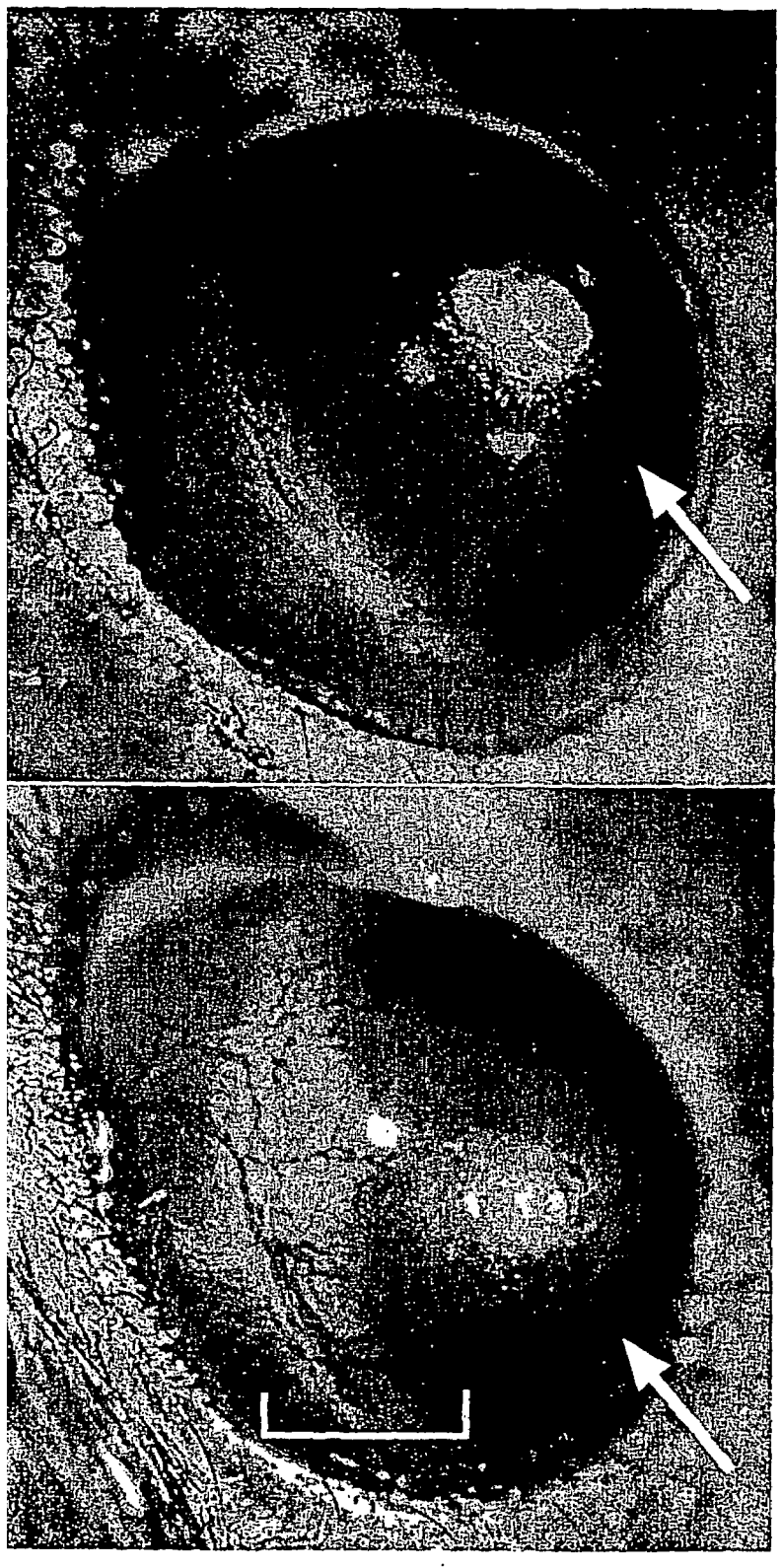
FIG. 5D displays photographs of the results of ocular angiogenesis studies wherein polymers containing IPAS antisense or sense oligonucleotides were implanted in to micropockets of the cornea, the area represented by an arrow, showing the antisense oligonucleotides caused neovascularization as indicated by the bracket.

Using similar methods, an analysis of the stimulation of blood vessel growth from the limbus region was recorded five normoxic days after implantation of micropellets. Significant ($p<0.001$ compared to sense or scrambled oligonucleotide controls) induction of neovascularization in the corneas of mice treated with the IPAS antisense oligonucleotide (FIGS. 5D, 5E) was observed. The physiological conditions of hypoxia which occur in the cornea, e.g., during sleep[14,15], can therefore induce vascular growth upon inhibition of IPAS expression.

EXAMPLE 9

Tumor Studies in Mice

Approximately $1\times10^6$ wild-type Hepa1c1c7 or stably IPAS-expressing hepatoma cells were implanted subcutaneously in an 8-10 week old male immunoincompetent SCID mouse. Six mice were in the treated group and seven mice were in the control group. Primary tumors were measured using digital calipers on the days indicated. Tumor volumes were calculated according to the formula: $width^2 \times length \times 0.52$ as is common in the art[24]. At day 18 after implantation, tumor tissues were resected and fixed with 4% formalin in phosphate-buffed saline for 24 hours. Tissues were imbedded in paraffin and stained with a rat anti-mouse antibody against CD31 antigen[24]. Positive signals were counted under a light microscope in at least 6 random fields at 40× magnification.

Figure 4B:
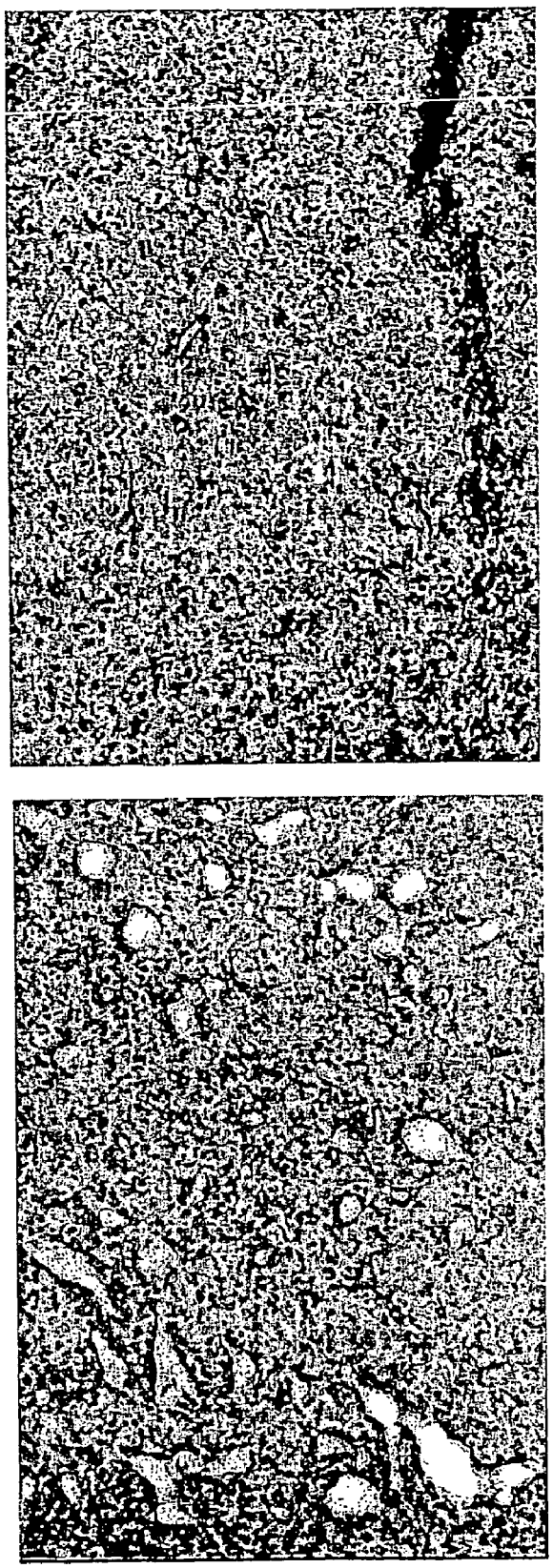
FIG. 4B shows vascular density by immunohistochemical staining for CD31 antigen expression
Figure 4C:
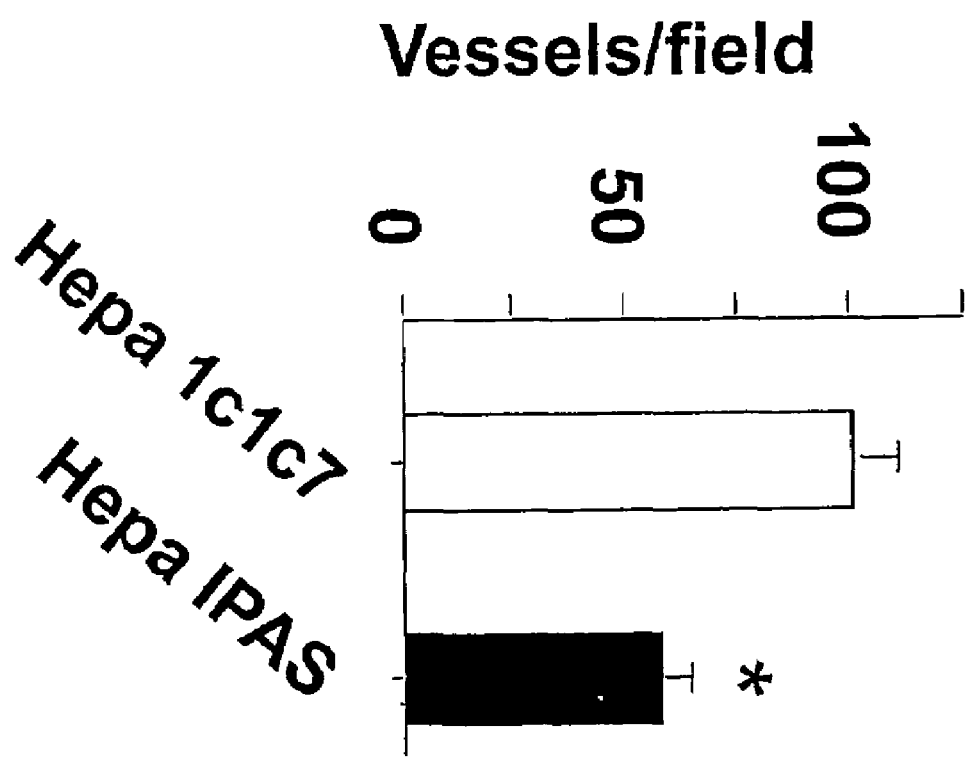
FIG. 4C represents a numerical analysis of vascular density with results obtained by counting under a light microscope, where an asterisk indicates (p<0.001) difference between wild-type and cell derived tumors.

The role of IPAS in negative regulation of angiogenesis was evaluated by determining both the growth rates and vascular density of the tumors formed following implantation. As shown in FIG. 4A, IPAS-expressing hepatoma cells produced tumors which showed a markedly slower growth rate than that of the wild-type cells ($p<0.001$-$0.01$ at all time points of observation). The tumors derived from the IPAS-expressing cells showed a significantly ($p<0.001$) reduced vascular density in comparison to the wild-type tumors, as assessed by staining tumor samples with CD31 antibodies (FIGS. 4B, 4C).

EXAMPLE 10

IPAS as a Pro-Angiogenic Treatment

An organism would be treated with antisense IPAS by any means appropriate and, if necessary, including any pharmaceutically acceptable carrier or adjuvant. Treatment may include such methods as topical application, injection, infusion, gene therapy, use of liposomes or controlled release mechanisms, and a variety of any and all other methods determined appropriate by the practitioner. Antisense IPAS would effectively inactivate IPAS and prevent conditional negative regulatory strategy. This would occur because IPAS would be prevented from forming a nonfunctional complex with HIF-1α. Such a mechanism is depicted in FIG. 5F. The mechanism relied upon for the present invention and depicted in FIG. 5F resembles the mechanism of repression of the function of MyoD and related bHLH differentiation factors by Id[20].

Treated regions of the organism may preferably include tissues exposed to hypoxia, such as the cornea or ischemic heart tissue. Following treatment, HIF-1α activity would no longer be suppressed and angiogenesis would proceed. Conditions that may benefit from treatment with IPAS antagonists according to the present invention include, but are not limited to, coronary heart disease, wound healing, stroke, and diabetic ulceration.

REFERENCES

1. Bunn, H. F. & Poyton, R. O. Oxygen sensing and molecular adaptation to hypoxia. *Physiol Rev* 76, 839-885 (1996).
2. Wenger, R. H. Mammalian oxygen sensing, signalling and gene regulation. *J. Exp. Biol.* 203, 1253-1263 (2000).
3. Krogh, A., Brown, M., Mian, I. S., Sjolander, K. & Haussler, D. Hidden Markov models in computational biology. Applications to protein modeling. *J. Mol. Biol.* 235, 1501-1531 (1994).
4. Wang, G. L., Jiang, B. H., Rue, E. A. & Semenza, G. L. Hypoxia-inducible factor 1 is a basic-helix-loop-helix-PAS heterodimer regulated by cellular O2 tension. *Proc Natl Acad Sci USA* 92, 5510-5514 (1995).
5. Ema, M. et al. A novel bHLH-PAS factor with close sequence similarity to hypoxia-inducible factor 1alpha regulates the VEGF expression and is potentially involved in lung and vascular development. *Proc Natl Acad Sci USA* 94, 4273-4278 (1997).
6. Tian, H., McKnight, S. L. & Russell, D. W. Endothelial PAS domain protein 1 (EPAS1), a transcription factor selectively expressed in endothelial cells. *Genes Dev* 11, 72-82 (1997).
7. Semenza, G. L. HIF-1 and human disease: one highly involved factor. *Genes Dev* 14, 1983-1991 (2000).
8. Kallio, P. J., Wilson, W. J., O'Brien, S., Makino, Y. & Poellinger, L. Regulation of the hypoxia-inducible transcription factor 1alpha by the ubiquitin-proteasome pathway. *J Biol Chem* 274, 6519-6525 (1999).
9. Maxwell, P. H. et al. The tumour suppressor protein VHL targets hypoxia-inducible factors for oxygen-dependent proteolysis [see comments]. *Nature* 399, 271-275 (1999).
10. Wiesener, M. S. et al. Induction of endothelial PAS domain protein-1 by hypoxia: characterization and comparison with hypoxia-inducible factor-1a. *Blood* 92, 2260-2268 (1998).
11. Li, H., Ko, H. P. & Whitlock, J. P. Induction of phosphoglycerate kinase 1 gene expression by hypoxia. Roles of Arnt and HIF1 alpha. *J Biol Chem* 271, 21262-21267 (1996).
12. Forsythe, J. A. et al. Activation of vascular endothelial growth factor gene transcription by hypoxia-inducible factor 1. *Mol. Cell Biol.* 16, 4604-4613 (1996).
13. Poellinger, L. in *Inducible gene expression* (ed. Baeuerle, P. A.) 177-205 (Birkhäuser, Boston, 1995).
14. Thakur, A., Willcox, M. D. & Stapleton, F. The proinflammatory cytokines and arachidonic acid metabolites in human overnight tears: homeostatic mechanisms. *J. Clin. Immunol.* 18, 61-70 (1998).
15. Sack, R. A., Beaton, A. R. & Sathe, S. Diurnal variations in angiostatin in human tear fluid: a possible role in prevention of corneal neovascularization. *Curr. Eye. Res* 18, 186-193 (1999).
16. Gradin, K. et al. Functional interference between hypoxia and dioxin signal transduction pathways: competition for recruitment of the Arnt transcription factor. *Mol Cell Biol* 16, 5221-5231 (1996).
17. Ravi, R. et al. Regulation of tumor angiogenesis by p53-induced degradation of hypoxia-inducible factor 1. *Genes Dev.* 14, 34-44 (2000).
18. Zundel, W. et al. Loss of PTEN facilitates HIF-1-mediated gene expression. *Genes Dev.* 14, 391-396 (2000).
19. Li, J. et al. PR 39, a peptide regulator of angiogenesis. *Nat. Med.* 6, 49-55 (2000).
20. Norton, J. D., Deed, R. W., Craggs, G. & Sablitzky, F. Id helix-loop-helix protein in cell growth and differentiation. *Trends Cell Biol.* 8, 58-65 (1998).
21. Eddy, S. R. Multiple alignment using hidden Markov models. *Ismb* 3, 114-120 (1995).
22. Tanimoto, K., Makino, Y., Pereira, T., and Poellinger, L. Mechanism of regulation of the hypoxia-inducible factor-1 by the von Hippel-Lindau tumor suppressor protein. *EMBO J.* 19, 4298-4309 (2000).
23. Bertilsson, G. et al. Identification of a human nuclear receptor defines a new signaling pathway for CYP3A induction. *Proc. Natl. Acad. Sci. USA* 95, 12208-12213 (1998).
24. Cao, R. et al. Suppression of aniogenesis by a novel inhibitor, K1-5, generated by plasmin-mediated proteolysis. *Proc. Natl. Acad. Sci. USA* 96, 5728-5733 (1999).

What is claimed is:

1. A pharmaceutical composition, comprising the sequence of SEQ ID NO:5 and at least one pharmaceutical carrier.

2. A pharmaceutical composition, comprising a sequence having 95% homology to the sequence of SEQ ID NO:5 and at least one pharmaceutical carrier.

3. A pharmaceutical composition, comprising a sequence having 90% homology to the sequence of SEQ ID NO:5 and at least one pharmaceutical carrier.

4. A pharmaceutical composition, comprising a sequence having 85% homology to the sequence of SEQ ID NO:5 and at least one pharmaceutical carrier.

5. A pharmaceutical composition, comprising a sequence having 80% homology to the sequence of SEQ ID NO:5 and at least one pharmaceutical carrier.

6. A pharmaceutical composition, comprising a sequence having 75% homology to the sequence of SEQ ID NO:5 and at least one pharmaceutical carrier.

7. A pharmaceutical composition, comprising a sequence having 70% homology to the sequence of SEQ ID NO:5 and at least one pharmaceutical carrier.

8. A pharmaceutical composition according to claim 1, further comprising at least one item selected from the group consisting of adjuvants, and diluents.

9. A plasmid comprising the sequence of SEQ ID NO: 5.

10. An isolated host cell expressing the protein encoded by SEQ ID NO:5.

* * * * *

SEQUENCE LISTING

```
<160> NUMBER OF SEQ ID NOS: 5

<210> SEQ ID NO 1
<211> LENGTH: 307
<212> TYPE: PRT
<213> ORGANISM: Mus sp.

<400> SEQUENCE: 1

Met Ala Leu Gly Leu Gln Arg Val Arg Ser Asn Thr Glu Leu Arg Lys
1               5                   10                  15

Glu Lys Ser Arg Asp Ala Ala Arg Ser Arg Arg Ser Gln Glu Thr Glu
            20                  25                  30
```

```
Val Leu Tyr Gln Leu Ala His Thr Leu Pro Phe Ala Arg Gly Val Ser
         35                  40                  45

Ala His Leu Asp Lys Ala Ser Ile Met Arg Leu Thr Ile Ser Tyr Leu
 50                  55                  60

Arg Met His Arg Leu Cys Ala Ala Gly Gly Lys Arg Gly Arg Ala Thr
 65                  70                  75                  80

Gly Arg Leu Leu Pro Glu Gly Pro Gly Gly Phe Arg His Gly Thr His
                 85                  90                  95

Arg Arg Gly Arg His Gly Leu Pro Val Gly Lys Cys Gln Gln Ala Pro
             100                 105                 110

Gly Pro Gln Ser Val Asp Leu Cys Ser Ser Leu Ile His Asn Pro
         115                 120                 125

Thr Pro Gly Thr Asn Phe Ser Leu Glu Leu Ile Gly His Ser Ile Phe
 130                 135                 140

Asp Phe Ile His Pro Cys Asp Gln Glu Glu Leu Gln Asp Ala Leu Thr
145                 150                 155                 160

Pro Arg Pro Asn Leu Ser Lys Lys Leu Glu Ala Pro Thr Glu Arg
                 165                 170                 175

His Phe Ser Leu Arg Met Lys Ser Thr Leu Thr Ser Arg Gly Arg Thr
                 180                 185                 190

Leu Asn Leu Lys Ala Ala Thr Trp Lys Val Leu His Cys Ser Gly His
         195                 200                 205

Met Arg Ala Tyr Lys Pro Pro Ala Gln Thr Ser Pro Ala Gly Ser Pro
 210                 215                 220

Arg Ser Glu Pro Pro Leu Gln Cys Leu Val Leu Ile Cys Glu Ala Ile
225                 230                 235                 240

Pro Gln Leu Pro Phe His Asp Gly Ala Thr Leu Gly Leu Pro Gln Glu
                 245                 250                 255

Lys Thr Pro Ile Ser Thr Leu Phe Thr Pro Leu Trp Lys Ala Leu Leu
                 260                 265                 270

Cys Leu Val Lys Arg Trp Pro Val Gln Val Leu Gln Gly Lys Gly Thr
         275                 280                 285

Glu Ser Ser Leu Pro Ser Trp Val Leu Trp Ala Leu Asn Arg Lys Asn
 290                 295                 300

Cys Pro Gly
305
```

<210> SEQ ID NO 2
<211> LENGTH: 1032
<212> TYPE: DNA
<213> ORGANISM: Mus sp.

<400> SEQUENCE: 2

```
ggcacgaggg ccatggcgtt ggggctgcag cgcgtgaggt cgaacaccga gctgcggaag    60
gagaagtcgc gggacgcggc ccgcagccgg cgcagccagg agacggaggt gctgtaccag   120
ctggcgcaca ctctgccctt tgcgcgcggc gtcagcgcgc acctggacaa ggcctccatc   180
atgcgcctca caatcagcta cctgcgcatg caccgcctct cgcagcaggt ggaaaaagg   240 gggagagcca ctggacgcct gctacctgaa ggccctggag ggtttcgtca tggtactcac   300
cgccgaggga gacatggctt acctgtcgga aaatgtcagc aagcacctgg gcctcagtca   360
gtggacctct gttcctcctc cctgatacat aaccccactc ctggtaccaa tttctctctg   420
gagctcattg acacagtat ctttgatttt atccatccct gtgaccaaga ggaacttcaa    480
gacgccctga cccccaggcc gaacctgtca agaagaagc tggaagcccc aacagagcgc   540
```

-continued

| | |
|---|---|
| cactttccc tgcgaatgaa gagcacgctc accagcagag ggcgcacgct caacctcaaa | 600 |
| gcggccacct ggaaggtgct gcactgctca ggacatatga gggcctacaa gccccctgca | 660 |
| cagacttccc ctgccgggag ccctcgctcc gagcctcccc tgcaatgcct ggtgcttatc | 720 |
| tgtgaagcca tcccccagct cccccttccac gatggtgcta ctctgggtct tccacaggag | 780 |
| aagactccca tctctaccct attcacccct ctttggaagg cactactttg tcttgtcaag | 840 |
| aggtggcctg ttcaggtgct acaggggaaa gggactgaat cctctctccc ctcatgggtg | 900 |
| ttgtgggccc ttaaccggaa aaattgtcct ggctaggagg gagtgaagga catggcccag | 960 |
| ctatccttag cccagaaacc cacaaatgtc tccaaaacca cataaagac ctctccttgt | 1020 |
| taggcaccag ag | 1032 |

<210> SEQ ID NO 3
<211> LENGTH: 25
<212> TYPE: DNA
<213> ORGANISM: Mus sp.

<400> SEQUENCE: 3
tcacgcgctg cagccccaac gccat         25

<210> SEQ ID NO 4
<211> LENGTH: 25
<212> TYPE: DNA
<213> ORGANISM: Mus sp.

<400> SEQUENCE: 4
atggcgttgg ggctgcagcg cgtga         25

<210> SEQ ID NO 5
<211> LENGTH: 1032
<212> TYPE: DNA
<213> ORGANISM: Mus sp.

<400> SEQUENCE: 5

| | |
|---|---|
| tcggtgttcg acctcacgcg ctgcagcccc aacgccatgg ccctcgtgcc cctggctgcg | 60 |
| ccggctgcgg gccgcgtccc gcgacttctc cttccgcagc gccgcgcgca aagggcagag | 120 |
| tgtgcgccag ctggtacagc acctccgtct tagctgattg tgaggcgcat gatggaggcc | 180 |
| ttgtccaggt gcgcgctgac tggctctccc ccttttttcca cctgctgcgc agaggcggtg | 240 |
| catgcgcagg gtgagtacca tgacgaaacc ctccagggcc ttcaggtagc aggcgtccag | 300 |
| ccaggtgctt gctgacattt tccgacaggt aagccatgtc tccctcggcg gagtgggggtt | 360 |
| atgtatcagg gaggaggaac agaggtccac tgactgaggc aaaatcaaag atactgtgtc | 420 |
| caatgagctc cagagagaaa ttggtaccag gcctggggg tcagggcgtc ttgaagttcc | 480 |
| tcttggtcac agggatggat gggaaaagtg gcgctctgtt ggggcttcca gcttcttctt | 540 |
| tgacaggttc tttgaggttg agcgtgcgcc ctctgctggt gagcgtgctc ttcattcgca | 600 |
| ttgtaggccc tcatatgtcc tgagcagtgc agcaccttcc aggtggccgc ggggaggctc | 660 |
| ggagcgaggg ctcccggcag gggaagtctg tgcaggggc gtggaagggg agctgggga | 720 |
| tggcttcaca gataagcacc aggcattgca aaggtagaga tgggagtctt ctcctgtgga | 780 |
| agacccagag tagcaccatc caggccacct cttgacaaga caaagtagtg ccttccaaag | 840 |
| aggggtgaat cacccatgag gggagagagg attcagtccc tttcccctgt agcacctgaa | 900 |
| tccttcactc cctcctagcc aggacaattt ttccggttaa gggcccacaa tggttttgga | 960 |

```
-continued gacatttgtg ggtttctggg ctaaggatag ctgggccatg ctctggtgcc taacaaggag    1020
aggtctttat gg                                                        1032
```